United States Patent [19]
Halczenko et al.

[11] Patent Number: 4,548,941
[45] Date of Patent: Oct. 22, 1985

[54] 1,5-METHANO-1H-4-BENZAZONINE DICARBOXYLATES, PROCESS FOR PREPARING AND USE AS CALCIUM BLOCKERS

[75] Inventors: Wasyl Halczenko, Hatfield; George D. Hartman, Lansdale, both of Pa.

[73] Assignee: Merck & Co., Inc., Rahway, N.J.

[21] Appl. No.: 635,953

[22] Filed: Jul. 30, 1984

[51] Int. Cl.[4] .............................. C07D 221/22
[52] U.S. Cl. .................... 514/295; 546/93; 544/60; 544/126; 544/361
[58] Field of Search ..................... 546/93; 424/266

[56] References Cited
U.S. PATENT DOCUMENTS
4,024,265  5/1977  Bastian .......................... 546/93

OTHER PUBLICATIONS

Schramm et al., "Novel Dihydropyridines with Positive Intropic Action Through Activation of $Ca^{+2}$ Channels", *Nature,* 303, 535–537, (6/9/83).
Bossert et al., "4-Aryldihydropyridines, A New Class of Highly Active Calcium Antagonists", *Angew. Chem. Int. Ed. English* 20, 762–769 (1981).

*Primary Examiner*—Henry R. Jiles
*Assistant Examiner*—Patricia Ann Bucci
*Attorney, Agent, or Firm*—Salvatore C. Mitri; Joseph F. DiPrima; Michael C. Sudol

[57] ABSTRACT

There are disclosed novel substituted and bridged pyridines which are useful as calcium channel blockers.

7 Claims, No Drawings

1,5-METHANO-1H-4-BENZAZONINE DICARBOXYLATES, PROCESS FOR PREPARING AND USE AS CALCIUM BLOCKERS

BACKGROUND OF THE INVENTION

Substituted dihydropyridines are known to be useful for reducing blood pressure, effecting dilation of the coronary vessels, and preventing urospasms. Typical of such substituted dihydropyridines are those disclosed in U.S. Pat. Nos. 3,923,818; 3,905,970; 4,044,141; 4,237,137; and, 4,285,955. The substituted dihydropyridines disclosed in these patents do not include bridged ring structures.

Weller et al., [J. Org. Chem., 48, pp. 3061-7 (1983)] disclose 1'-methylspiro[benzofuran-3(2H),4'-piperidine] as a substructure of morphine which is an early intermediate in a general synthesis of morphine but not possessing exceptional analgesic activity. Weller et al. also teach the preparation of spiro [benzofuran-3(2H),4'-(1'H)-pyridines as potential intermediates in a synthesis of morphine but no biological activity of these compounds is reported.

Goldman [Angew. Chem. Int. Ed. Engl., 20, pp. 779-780 (1981)] teaches the preparation of spiro[benzothiophene-1-oxide,4-pyridines] as an intermediate in the preparation of 4,4-disubstituted 1,4-dihydropyridines.

SUMMARY OF THE INVENTION

This invention is directed to novel substituted and bridged pyridines and derivatives thereof and to methods for preparing such compounds. This invention is also directed to pharmaceutical compositions and methods of treatment for cardiovascular disorders in which high cellular concentration of $Ca^{++}$ is a factor.

DETAILED DESCRIPTION OF THE INVENTION

The specific substituted and bridged pyridine compounds of this invention are represented by the following general structural formula (I):

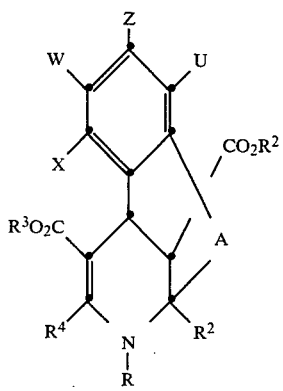

wherein: A is

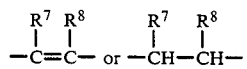

wherein $R^7$ and $R^8$ independently are hydrogen or $C_1-C_8$ alkyl;

R is hydrogen, $C_1-C_8$ alkyl or benzyl;

$R^1$ and $R^4$ independently are hydrogen, $C_1-C_8$ alkyl, $C_2-C_8$ alkenyl, $C_3-C_8$ cycloalkyl, $C_1-C_8$ hydroxyalkyl;

$R^2$ and $R^3$ independently are $C_1-C_8$ alkyl, $C_2-C_8$ alkenyl, $C_3-C_8$ cycloalkyl, $C_1-C_8$ hydroxyalkyl, $C_1-C_8$ dihydroxyalkyl, $C_2-C_8$ alkoxyalkyl, $C_3-C_8$ alkoxy(alkoxyalkyl), $C_1-C_8$ aminoalkyl wherein the amino group is $NR^5R^6$ in which $R^5$ and $R^6$ independently are hydrogen, $C_1-C_8$ alkyl, $C_7-C14$ phenylalkyl or $R^5$ and $R^6$ together with the N atom form a 5 or 6 membered heterocycle selected from the group consisting of piperidinyl, morpholinyl, thiomorpholinyl, pyrrolidinyl, piperazinyl or $N'-C_1-C_4$-alkyl piperazinyl; and X, W, Z and U independently are hydrogen, $C_1-C_8$ alkyl, $C_1-C_8$ alkoxy, $C_7-C_{14}$ alkoxyphenyl, phenoxy or $NR^9R^{10}$ wherein $R^9$ and $R^{10}$ independently are hydrogen, or $C_1-C_8$ alkyl, provided that at least two of X, W, Z and U are hydrogen; and pharmaceutically acceptable salts thereof.

The preferred compounds of this invention are those represented by the general structural formula (I) wherein: A is

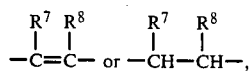

wherein $R^7$ and $R^8$ are hydrogen;

R is hydrogen;

$R^1$ and $R^4$ independently are hydrogen or $C_1-C^8$ alkyl;

$R^2$ and $R^3$ independently are $C_1-C_8$ alkyl;

X, W, Z and U independently are hydrogen, $C_1-C_8$ alkoxy, or phenoxy, provided that at least two of X, W, Z and U are hydrogen The most preferred compounds of this invention are those preferred compounds wherein: $R^1$ and $R^4$ independently are $C_1-C_8$ alkyl; and X, Z and U are hydrogen; and W is $C_{1-8}$ alkoxy.

The compounds of this invention possess asymmetric centers and thus exist in different isomeric forms. All such forms are included within the scope of this invention. Specifically, the compounds have an asymmetric center at the carbon atom to which the ester moiety, $CO_2R^2$, is attached. Whenever the ester moiety is below the plane of the piperidine ring (i.e. down) that stereochemical configuration is denoted as the alpha ($\alpha$)-isomer. Similarly, whenever that ester moiety is above the plane of the piperidine plane (i.e. up) that stereochemical configuration is denoted as the beta ($\beta$)-isomer.

Illustrative of the compounds of this invention are the following compounds of the Formula (I) which are the $\alpha$-isomer, $\beta$-isomer or a mixture thereof:

(1) Dimethyl 4,5-dihydro-10-methoxy-3,5-dimethyl-1,5-methano-1H-4-benzazonine-2,12-dicarboxylate [Formula (I) where A is $-CH=CH-$, R is hydrogen, $R^1$, $R^2$, $R^3$ and $R^4$ are methyl, W is methoxy and X, Z and U are hydrogen]; and (2) Dimethyl 4,5,6,7-tetrahydro-10-methoxy-3,5-dimethyl-1,5-methano-1H-4-benzazonine-2,12-dicarboxylate [Formula (I) where A is $-CH_2-CH_2-$, R is hydrogen, $R^1$, $R^2$, $R^3$ and $R^4$ are methyl, W is methoxy and X, Z and U are hydrogen].

The pharmaceutically acceptable salts are those acid addition salts of non-toxic, pharmaceutically acceptable acids and include salts of inorganic acids such as hydrochloric, hydrobromic, hydroiodic, phosphoric, sulfuric, nitric and the like, and organic acids such as trifluoroacetic and trichloroacetic and the like and include acids related to the pharmaceutically acceptable salts listed in Journal of Pharmaceutical Science, 66, 2 (1977) and incorporated herein by reference.

The compounds of this invention are conveniently prepared from known or readily obtainable starting materials utilizing the general synthetic pathway described below:

general Hantzsch reaction conditions to afford the aryl dihydropyridine compound (2).

The aryl dihydropyridine (2) is then treated at between −10° and 50° C., preferably at −5° to 0° C., with between 1 and 10 equivalents, preferably a 2-fold excess, of a protic acid in an inert solvent to yield the cyclized compound (3). Examples of such anhydrous

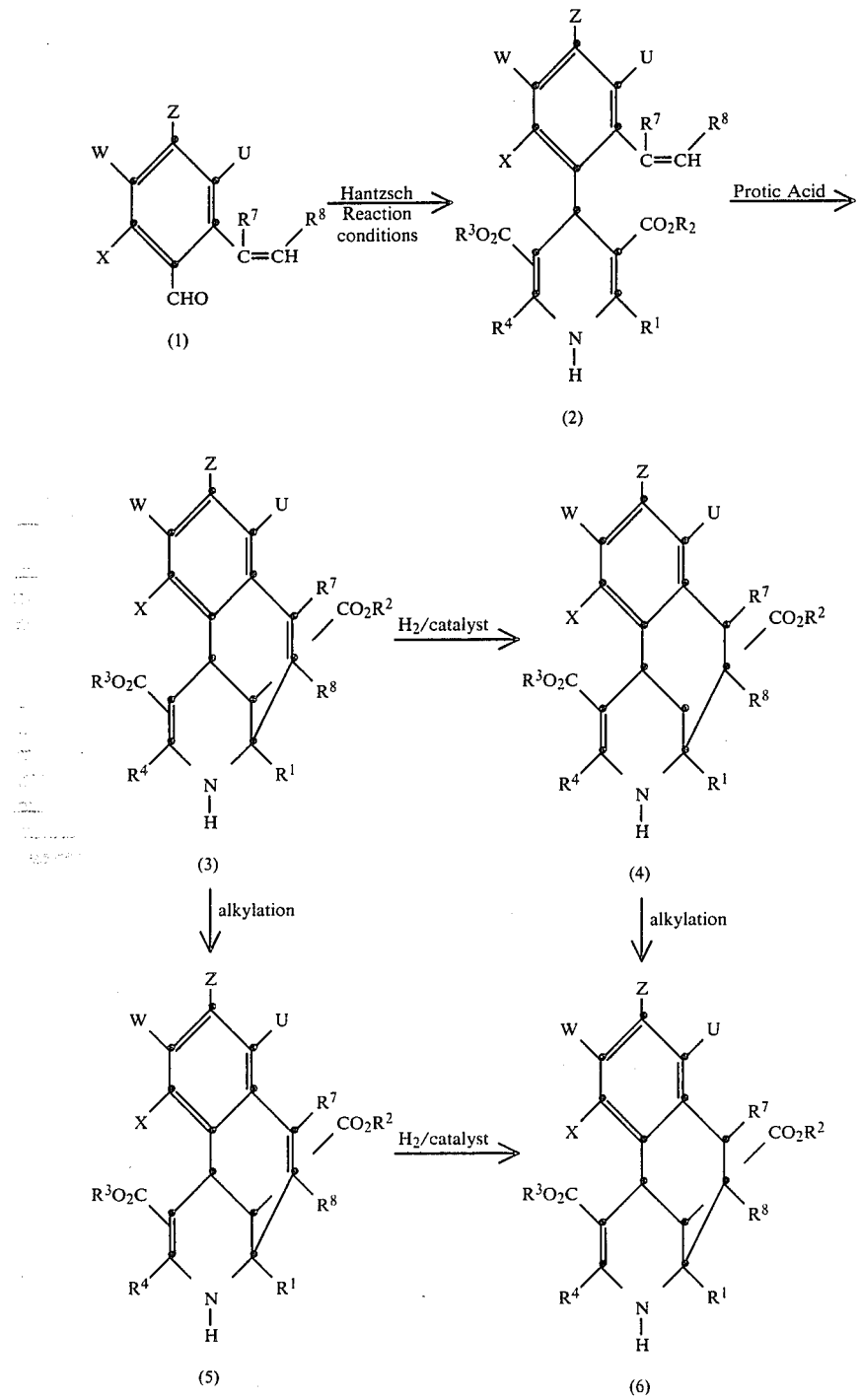

The aryl aldehyde (1), wherein $R^7$, $R^8$, X, W, Z and U are described above, is reacted with an appropriately substituted 3-aminopropenoate, such as methyl 3-aminocrotonate, and an appropriately substituted 3-oxopropanoate, such as methyl acetoacetate, under the protic acids include gaseous hydrogen chloride and gaseous hydrogen bromide. Exemplifying the inert solvents employed in this cyclization reaction are ethers, chlorinated hydrocarbons, and aromatic hydrocarbons.

Preferred solvents are methylene chloride, chloroform, benzene and toluene.

The cyclized compound (3) is either: (A) first hydrogenated under standard condition to give compound (4) which is then alkylated under standard conditions to yield the compound (6); or (B) first alkylated under standard conditions to afford the compound (5) which is then hydrogenated under standard conditions to give (6).

As indicated above, the compounds of this invention are useful as calcium channel blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory system; (vi) useful antihypercholesterolemic and antilipademic action; (vii) protection of the ischemic myocardium; (viii) inhibition of irritable bowel syndrome and esophageal spasm; and, (ix) inhibition of migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace tritiated nitrendepine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration; e.q., as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., nitroglycerine tablets, lactose tablets, and the like, for rapid dissolution or high molecular weight methylcellulose tablets, carboxymethylcellulose tablets, and the like, for slower, time-releasing delivery; or, (c) for parenteral administration; e.g., dissolved or dispersed in a suitable liquid carrier or emulsified. The pharmaceutical preparations thus described are made following the conventional techniques of the pharmaceutical chemist as appropriate to the desired end product.

The ratio of active compound to compounding ingredients, i.e., carrier, diluent, etc., will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for obtaining the compounds and compositions of the invention, but are not to be construed as being limitative of the invention. Unless otherwise indicated, all temperatures are in °C.

EXAMPLE 1

Preparation of Dimethyl 4,5-dihydro-10-methoxy-3,5-dimethyl-1,5-methano-1H-4-benzazonine-2,12-dicarboxylate (a) 2-Bromo-5-methoxybenzaldehyde ethylene glycol acetal (1a)

To a solution of 2-bromo-5-methoxybenzaldehyde (93 mmol) in benzene (125 ml) was added ethylene glycol (110 mmol) and p-toluenesulfonic acid monohydrate (100 mg) and the reaction mixture refluxed for 3 hours with azeotropic removal of water. The reaction mixture was cooled, extracted with 10% aqueous sodium hydroxide ($2 \times 50$ ml), water ($5 \times 30$ ml) and brine, dried over anhydrous sodium sulfate and filtered. The filtrate was concentrated in vacuo to afford the Compound 1a.

(b) 2-[2-(1,3-dioxalanyl)]-4-methoxybenzaldehyde (1b)

To the Compound 1a (10 mmol) in dry tetrahydrofuran (15 ml) at $-78°$ C. under nitrogen was added a solution of n-butyllithium (10 mmol) in hexane dropwise. The reaction mixture was stirred for an additional 30 minutes and then a solution of N-formylpiperidine (11 mmol) in tetrahydrofuran (5 ml) was added dropwise. The reaction mixture was stirred for an additional 2 hours and allowed to warm to ambient temperature overnight. The reaction mixture, cooled in ice, was quenched with saturated aqueous ammonium chloride (10 ml) and diluted with diethyl ether (125 ml). The organic phase was washed with saturated aqueous ammonium chloride ($3 \times 25$ ml) and brine, dried over anhydrous sodium sulfate and filtered. The filtrate was concentrated in vacuo to afford the Compound 1b as a yellow oil.

(c) 2-[2-(1,3-dioxalanyl)]-4-methoxystyrene (1c)

To triphenylphosphonium methylbromide (12.5 mmol) suspended in dry tetrahydrofuran (20 ml) at $-78°$ C. under nitrogen was added a solution of n-butyllithium (12.5 mmol) in hexane dropwise and the reaction mixture allowed to warm to ambient temperature over 2.5 hours. A solution of the Compound 1b (10 mmol) in tetrahydrofuran (15 ml) was added dropwise to the reaction mixture at $0°$-$5°$ C. and then the reaction mixture was allowed to warm to ambient temperature overnight. The reaction mixture was diluted with methylene chloride (50 ml) and then the organic phase passed through a pad of silica gel and the silica gel pad washed with methylene chloride (5×50 ml). The combined organic phases were concentrated in vacuo and the residue purified by flash chromatography on silica gel eluted with hexane: ethyl acetate (85:15) to provide the Compound 1c as an oil (R$_f$=0.3).

(d) 2-Ethenyl-5-methoxybenzaldehyde (1d)

To the Compound 1c (3 mmol) in dry acetone (15 ml) was added p-toluenesulfonic acid and the resulting solution let stand at ambient temperature for 24 hours. The solvent was removed in vacuo, the residue diluted with diethyl ether (50 ml), washed with saturated aqueous sodium bicarbonate (2×25 ml) and brine, dried over anhydrous sodium sulfate and filtered. The filtrate was concentrated in vacuo to give the Compound 1d as a yellow oil.

(e) Dimethyl 2,6-dimethyl-4-[2-(2-ethenyl-5-methoxy)phenyl]-1,4-dihydropyridine-3,5-dicarboxylate (1e)

To the Compound 1d (49 mmol) in dry methanol (50 ml) was added methyl 3-aminocrotonate (49 mmol), methyl acetoacetate (49 mmol) and concentrated ammonium hydroxide (1 ml) and the resulting solution was heated to reflux under nitrogen for 4 days. The solvent was removed in vacuo and the residue triturated with diethyl ether (25 ml) to give the Compound 1e as a pale yellow solid (m.p. 141°-3° C.). Additional Compound 1e was recovered from the diethyl ether extract.

(f) Dimethyl 4,5-dihydro-10-methoxy-3,5-dimethyl-1,5-methano-1H-4-benzazonine-2,12α-dicarboxylate (1f)

To the Compound 1e (5.6 mmol) in chloroform cooled to 0°-5° C. was added excess gaseous hydrogen chloride over 45 minutes. The reaction mixture was allowed to stand at ambient temperature for 24 hours. The reaction mixture was diluted with ice-water (35 ml), neutralized with concentrated aqueous ammonium hydroxide, and extracted with chloroform (3×50 ml). The combined organic extracts were washed with brine, dried over anhydrous sodium sulfate and filtered. The solvent was removed in vacuo and the residue triturated with hexane: diethyl ether (1:2, 2×20 ml) and the supernatants combined. The solvent was removed in vacuo and the residue purified by flash chromatography on silica gel eluted with hexane:diethyl ether (1:2) to afford the Compound 1f as a tan solid (R$_f$=0.3, m.p. 154°-5° C.).

EXAMPLE 2

Preparation of Dimethyl 4,5,6,7-tetrahydro-10-methoxy-3,5-dimethyl-1,5-methano-1H-4-benzazonine-2,12α-dicarboxylate To a solution of the Compound 1f (0.028 mmol) in absolute ethanol (2 ml) was added 5% palladium on carbon catalyst (1 mg) and the mixture hydrogenated at 27 pounds per square inch (psi) in a micro-Parr apparatus for 2.5 hours. The catalyst was removed by filtration and the solvent removed in vacuo. The residue was diluted with methylene chloride:methanol (97:3, 2 ml) which was passed through a pad of silica gel. The silica gel pad was washed with methylene chloride:methanol (97:3, 20 ml). The solvent was removed in vacuo to afford an oil which crystallized on standing to yield the desired compound in 90% purity by NMR.

EXAMPLES 3-16

Utilizing the general procedures of Example 1 and starting with the appropriately substituted material, the following compounds of the Formula (I) wherein A is $$\begin{array}{c} R^7 \ R^8 \\ | \ \ | \\ -C=C- \end{array}$$

are prepared.

| Compound No. | R | R$^1$ | R$^2$ | R$^3$ | R$^4$ | R$^7$ | R$^8$ | X | W | Z | U |
|---|---|---|---|---|---|---|---|---|---|---|---|
| 3 | H | Et | Me | Me | Et | H | H | H | H | H | H |
| 4 | H | Me | Et | Et | Me | Me | H | H | H | H | H |
| 5 | H | Me | Me | Me | Me | H | H | H | OC$_6$H$_5$ | H | H |
| 6 | Me | CH$_2$CH=CH$_2$ | Me | Me | Me | H | H | H | Me | H | H |
| 7 | H | CH$_2$OH | Me | Me | CH$_2$OH | H | H | H | OMe | H | H |
| 8 | H | Me | Et | Et | 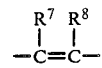 | Me | H | OMe | H | H | H |
| 9 | Me | Me | CH=CH$_2$ | CH=CH$_2$ | Me | H | H | H | OEt | H | H |
| 10 | H | Me | Me | ⌬ | Me | H | Me | H | H | Me | H |
| 11 | H | Me | CH$_2$OH | CH$_2$OH | Me | H | H | H | OC$_6$H$_5$ | H | H |
| 12 | H | Me | CH$_2$CH CH$_2$ \| \| OH OH | Me | Me | H | H | H | OC$_6$H$_5$ | H | H |
| 13 | H | Me | CH$_2$CH$_2$OCH$_2$CH$_2$OCH$_3$ | CH$_2$CH$_2$OCH$_2$CH$_2$OCH$_3$ | Me | H | H | H | NMe$_2$ | H | H |
| 14 | H | Me | CH$_2$NMe$_2$ | CH$_2$NMe$_2$ | Me | H | H | NMe$_2$ | H | H | H |
| 15 | H | Me | Me | CH$_2$—N⌬ | Me | H | H | H | H | H | Me |

-continued

| Compound No. | R | R¹ | R² | R³ | R⁴ | R⁷ | R⁸ | X | W | Z | U |
|---|---|---|---|---|---|---|---|---|---|---|---|
| 16 | H | Me | CH₂NCH₃ \| CH₂φ | Me | Me | H | H | H | Me | Me | H |

It should be noted that for the preparation of Compounds 7, 11, and 12 the hydroxyalkyl moiety is acylated with acetic anhydride prior to cyclization and then deacylated with sodium hydroxide.

EXAMPLES 17–19

Utilizing the general procedure of Example 2 and starting with the appropriate material, the following compounds of the Formula (I) wherein A is

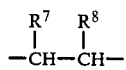

are prepared.

| Compound No. | R | R¹ | R² | R³ | R⁴ | R⁷ | R⁸ | X | W | Z | U |
|---|---|---|---|---|---|---|---|---|---|---|---|
| 17 | H | Et | Me | Me | Et | H | H | H | H | H | H |
| 18 | H | Me | Et | Et | Me | Me | H | H | H | H | H |
| 19 | H | Me | Me | Me | Me | H | H | H | OC₆H₅ | H | H |

EXAMPLE 20

As a specific embodiment of a composition of this invention the active ingredient such as dimethyl 4,5-dihydro-10-methoxy-3,5-dimethyl-1,5-methano-1H-4-benzazonine-2,12α-dicarboxylate, is formulated to yield 5000 compressed tablets, each containing 50 mg of the active ingredient as follows:

Active ingredient: 250 grams
Starch: 70 grams
Dibasic calcium phosphate hydrous: 500 grams
Calcium stearate: 2.5 grams

What is claimed is:

1. A compound represented by the general structural Formula (I):

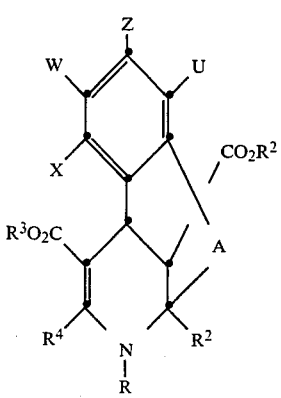

wherein:
A is $$-\overset{R^7}{\underset{|}{C}}=\overset{R^8}{\underset{|}{C}}-$$

wherein $R^7$ and $R^8$ independently are hydrogen or $C_1$–$C_8$ alkyl;

R is hydrogen or $C_1$–$C_8$ alkyl;

$R^1$ and $R^4$ independently are hydrogen, $C_1$–$C_8$ alkyl, $C_2$–$C_8$ alkenyl, $C_3$–$C_8$ cycloalkyl, $C_1$–$C_8$ hydroxyalkyl;

$R^2$ and $R^3$ independently are $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy(alkoxyalkyl), $C_1$–$C_8$ aminoalkyl wherein the amino group is $NR^5R^6$ in which $R^5$ and $R^6$ independently are hydrogen, $C_1$–$C_8$ alkyl, $C_7$–$C_{14}$ phenylalkyl; and X, W, Z and U are independently hydrogen, $C_1$–$C_8$ alkyl, $C_1$–$C_8$ alkoxy, $C_7$–$C_{14}$ alkoxyphenyl or phenoxy;

or a pharmaceutic ally acceptable salt thereof.

2. A compound according to claim 1 wherein:
A is $$-\overset{R^7}{\underset{|}{C}}=\overset{R^8}{\underset{|}{C}}-$$

in which $R^7$ and $R^8$ are hydrogen;
R is hydrogen;
$R^1$ and $R^4$ independently are hydrogen or $C_{1-8}$ alkyl;
$R^2$ and $R^3$ independently are $C_{1-8}$ alkyl; and
X, W, Z and U independently are hydrogen, $C_{1-8}$ alkoxy or phenoxy.

3. A compound according to claim 2 wherein:
$R^1$ and $R^4$ independently are $C_{1-8}$ alkyl;
X, Z and U are hydrogen; and
W is $C_{1-8}$ alkoxy.

4. A compound of claim 3 which is dimethyl 4,5-dihydro-10-methoxy-3,5-dimethyl-1,5-methano-1H-benzazonine-2,12α-dicarboxylate.

5. A pharmaceutical composition useful in the treatment of cardiovascular disorders in which a high cellular concentration of Ca++ is a factor, which comprises a nontoxic therapeutically effective amount of a compound according to claim 1 in an admixture with a pharmaceutically acceptable carrier.

6. A method of treatment for cardiovascular disorders in which a high cellular concentration of Ca++ is a factor which comprises administering to a subject in need of such treatment a non-toxic therapeutically effective amount of a compound according to claim 1.

7. A process for the preparation of a compound of claim 1 wherein:
A is

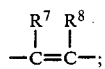
and
R is hydrogen
which comprises treating a compound represented by the following structural formula:
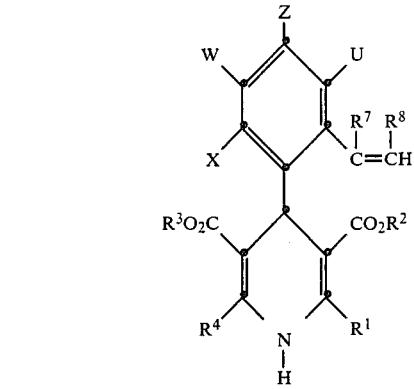
with a protic acid in an inert solvent.
* * * * *